United States Patent [19]
Hasegawa et al.

[11] Patent Number: 5,310,343
[45] Date of Patent: May 10, 1994

[54] ENDO-OSSEOUS IMPLANT

[76] Inventors: Jiro Hasegawa, 4-560 Komaki, Komaki-shi, Aichi-pref.; Bunkichi Azuma, 680-10 Aza Shimokawada, Ohaza Sanbongi, Nisshin-cho, Aichi-gun, Aichi-pref., both of Japan

[21] Appl. No.: 960,911

[22] Filed: Oct. 14, 1992

[51] Int. Cl.$^5$ .............................................. A61C 8/00
[52] U.S. Cl. ..................................................... 433/173
[58] Field of Search ..................... 433/173, 174, 201.1

[56] References Cited

U.S. PATENT DOCUMENTS

| | | | |
|---|---|---|---|
| 4,185,383 | 1/1980 | Heimke et al. | 433/173 |
| 4,631,031 | 12/1986 | Richter | 433/173 |
| 4,854,873 | 8/1989 | Linden | 433/173 |
| 4,934,935 | 6/1990 | Edwards | 433/174 |
| 5,087,199 | 2/1992 | Lazarof | 433/173 |
| 5,088,926 | 2/1992 | Lang | 433/173 |
| 5,108,289 | 4/1992 | Fukuyo | 433/173 |

FOREIGN PATENT DOCUMENTS

| | | |
|---|---|---|
| 164359 | 1/1989 | Japan . |
| 194846 | 1/1989 | Japan . |
| 194847 | 1/1989 | Japan . |
| 8900410 | 1/1989 | World Int. Prop. O. .......... 433/173 |

*Primary Examiner*—John G. Weiss
*Assistant Examiner*—Cindy A. Cherichetti
*Attorney, Agent, or Firm*—Lahive & Cockfield

[57] ABSTRACT

The present invention provides an improved endo-osseous implant which has sufficient binding force against occlusal pressure from every direction and does not cause any inflammation. The endo-osseous implant of the invention includes a large number of concaves on the circumference of a cylindrical main body embedded in dental alveoli. Each of the concaves has a shape of hemisphere or alternatively a shape of double hemisphere consisting of an upper hemisphere of greater diameter and a lower hemisphere of smaller diameter. Part of the cylindrical main body in contact with gingiva is covered with a polycrystal ceramic layer, and fine notches are further formed on the residual surface of the main body.

20 Claims, 3 Drawing Sheets

ENDO-OSSEOUS IMPLANT

BACKGROUND OF THE INVENTION

1. Field of the Invention

The present invention relates to a dental implant and more particularly to an endo-osseous implant inserted and embedded in gingiva and dental alveoli.

2. Description of the Related Art

Histologically stable adhesion of an endo-osseous implant to gingiva and dental alveoli against the occlusal pressure is essential for successful dental implant.

Some methods have been proposed to enhance the binding force of an endo-osseous implant: for example, forming grooves on the side wall of the implant as disclosed in Japanese Patent Laying-Open Gazette No. Hei-1-135346; and coating the implant with porous substance to increase the surface area in contact with the dental alveoli as disclosed in Japanese Patent Laying-Open Gazette No. Hei-1-164359.

In the former method, occlusal pressure from plural directions triggers unfavorable fracture of dental alveoli, which exceeds the physiological limit of absorption and neogenesis, adjacent to the grooves of the implant. Such fracture eventually causes removal of the implant from the dental alveoli. In the latter method, the larger surface area in contact with the dental alveoli ensures stable adhesion of the implant. Occlusion may, however, disturb the normal circulation of tissues inserted in the porous substance to necrose and putrefy the tissues and thereby cause inflammation of gingiva. The inflammation increases the internal pressure of the implant and lowers the adhesion of the implant to gingiva. In extreme cases, the implant is to be removed from the dental alveoli and gingiva by operation.

SUMMARY OF THE INVENTION

The object of the invention is to provide an improved endo-osseous implant which has sufficient binding force against occlusal pressure from every direction and does not cause any inflammation.

The above and other objects are realized by an endo-osseous implant having a large number of concave surfaces on the circumference of a cylindrical main body embedded in dental alveoli.

Each of the concavities may have a hemispherical shape or alternatively a double hemispherical shape consisting of an upper hemisphere of greater diameter and a lower hemisphere of smaller diameter. Part of the cylindrical main body in contact with gingiva may be covered with a polycrystal ceramic layer, and fine notches may further be formed on the residual surface of the main body.

The endo-osseous implant of the invention is protected from any loading until the implant securely adheres to dental alveoli through invasion of tissues of dental alveoli into the concave surfaces of the implant. The epithelial and fibrous tissues prevents fracture of dental alveoli due to occlusal pressure from exceeding the physiological limit of absorption and neogenesis. The endo-osseous implant of the invention thus has sufficient resistance against occlusal pressure from every direction.

These and other objects, features, aspects, and advantages of the present invention will become more apparent from the following detailed description of the preferred embodiment with the accompanying drawings.

DESCRIPTION OF THE PREFERRED EMBODIMENT

An endo-osseous implant embodying the invention is described according to the drawings.

Figure 2:
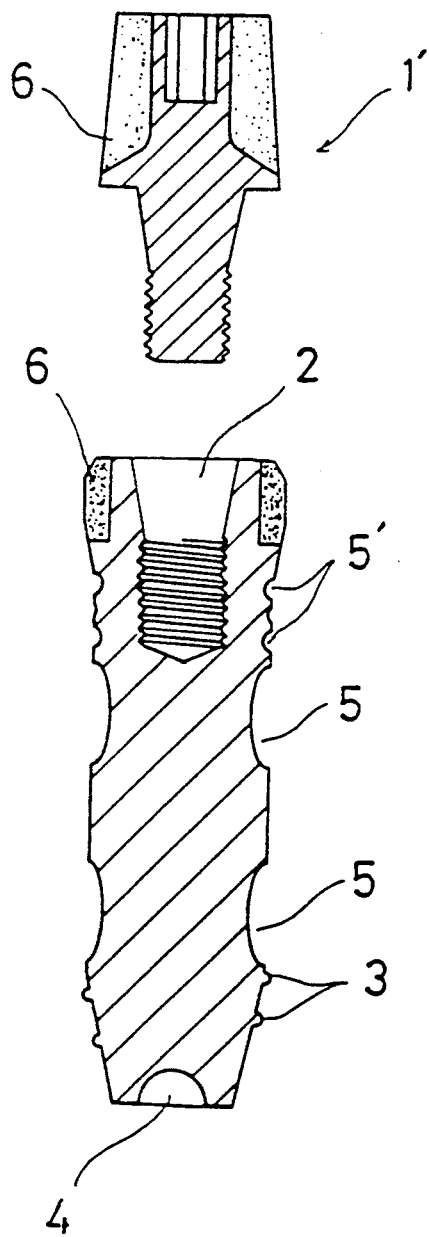
FIG. 2 is a cross sectional view of the endo-osseous implant of FIG. 1.
Figure 1:
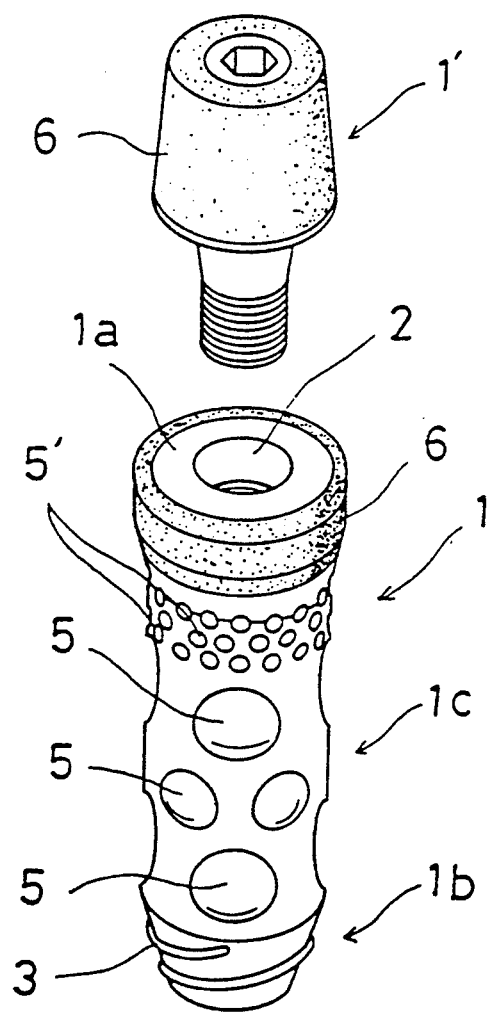
FIG. 1 is a perspective view illustrating an endo-osseous implant of the invention.
Figure 3:
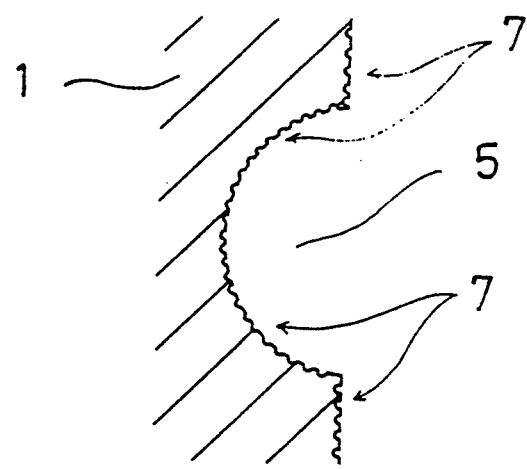
FIG. 3 is an enlarged view of a concavity formed on the circumference of the endo-osseous implant.

A cylindrical main body 1 of pure titanium (maximum diameter: 4.2 millimeter) includes: a female screw 2, which accommodates an end of an implanting instrument and a top 1' with a male screw for fixing a prosthesis is inserted in, at a head or a base end 1a thereof; and spiral threads 3 and a hemispherical concave 4 at a tapered tip or embedded end 1b thereof as shown in FIGS. 1 and 2. On the circumference of a shank 1c of the main body 1, there are a large number of hemispherical concavities 5, 5 of two different sizes: 2.4 millimeter and 1.5 millimeter in diameter. Three rows of concavities 5', 5' of a smaller diameter (0.5 millimeter) are closely formed on the shank 1c at the side of the base end 1a. The circumference of the top 1' and part of the main body 1 connecting with gingiva are respectively covered with a polycrystal ceramic layer 6. Fine notches 7 of several microns are formed on the whole surface of the main body 1 except the part covered with the polycrystal ceramic layer 6 as shown in FIG. 3.

The main body 1 of endo-osseous implant thus constructed is pressed into a hole having a hemispherical bottom protrusion, which is previously formed in dental alveoli, through rotation of an implanting instrument inserted in the female screw 2 of the main body 1. The hemispherical protrusion is securely fitted into the concave recess 4 to determine the position of the main body with respect to the dental alveoli. Any occlusal stress applied perpendicular to the implant is absorbed by the concave recess 4 since it has a wider surface area in contact with the dental alveoli. If no concave recess 4 is formed in the bottom of the implant, the implant could not absorb the force applied. The main body 1 is protected from undesirable loading for a certain time period, that is, until the main body securely adheres to dental alveoli (initial fixation). The top 1' is then screwed into the main body 1, and a prosthesis is attached to the top 1'.

The embedded endo-osseous implant closely adheres to dental alveoli in non-loading state, but fractures part of dental alveoli exposed to stress in loading state. Such fracture, however, does not cause any serious damage to the adhesion since absorption of the fractured osseous tissues physiologically balances neogenesis of the tissues.

During the initial fixation, osseous cells are newly generated on the surface of dental alveoli, and the large number of concaves of the endo-osseous implant ensure sufficiently large surface area in contact with the dental alveoli in every direction. The endo-osseous implant and dental alveoli are thus securely fixed to each other.

Although occlusal pressure fractures and absorbs the osseous tissues in the concave surfaces, newly generated tissues immediately the fractured tissues and prevent any serious inflammation. The fine notches on the surface of the implant also contribute to secure adhesion and strong affinity for the osseous tissues. The polycrystal ceramic layer covering over the upper portion of the implant in contact with gingiva is readily cut and worked in any shape suitable for the prosthesis. Furthermore, the ceramic layer conceals the metallic black of titanium and gives good appearance.

The sufficiently large surface area of the endo-osseous implant in contact with dental alveoli ensures high resistance against occlusal pressure from every direction. High affinity of the implant for dental alveoli and gingiva prevents any serious inflammation or after-effect of the operation.

The invention may be embodied in any other form without departing from the scope or spirit of essential characteristics thereof. The following are examples of modification.

Figure 4A:
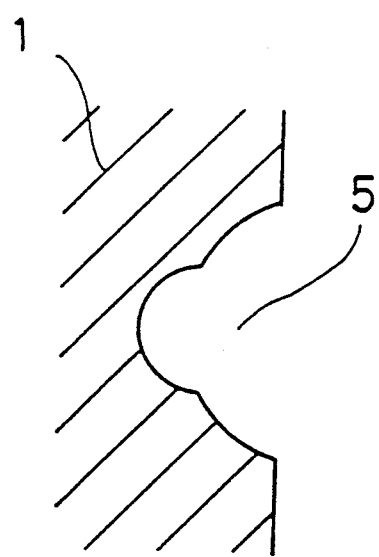
FIGS. 4A and 4B illustrate a concavity of another shape.
Figure 4B:
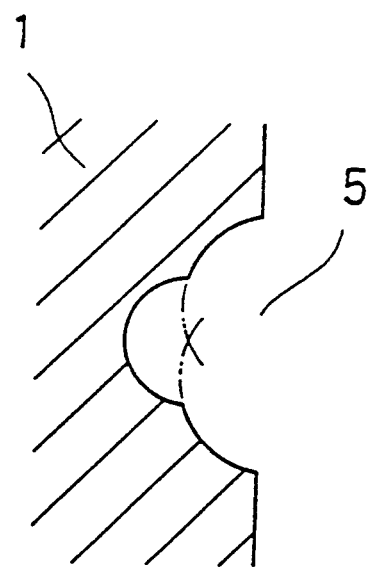
Figure 5A:
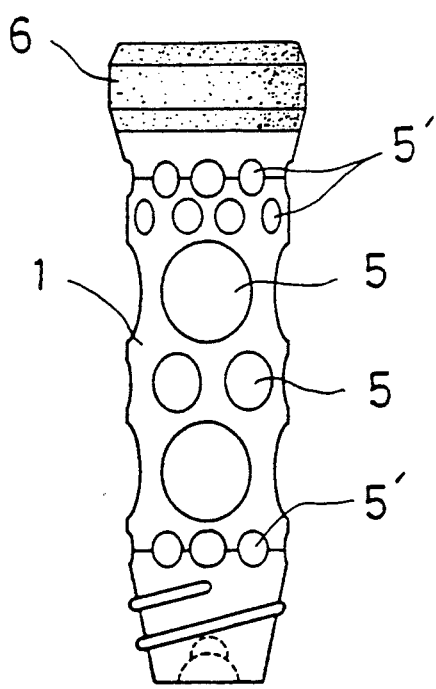
FIGS. 5A and 5B are front views illustrating other arrangements of concavities formed on the circumference of the endo-osseous implant.
Figure 5B:
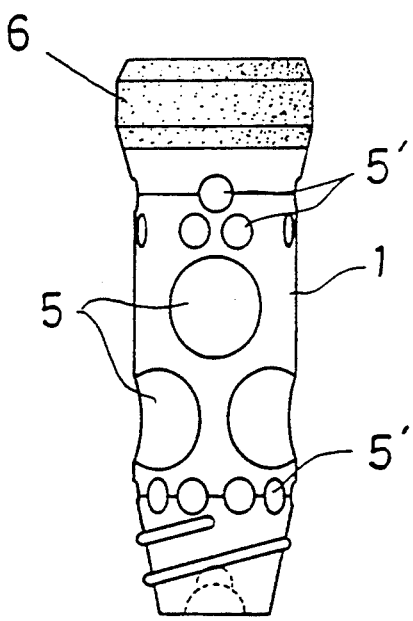

The main body and the top of the endo-osseous implant may integrally be formed though they are separately formed in the above embodiment. The arrangement, shape, depth, size, and the number of the concaves and the length of the main body are not limited to the above embodiment, but may be changed and modified accordingly. For example, each concavity may have a double hemispherical shape consisting of an upper hemisphere of greater diameter and a lower hemisphere of smaller diameter as shown in FIGS. 4A and 4B. The concavities may be arranged in different ways as shown in FIGS. 5A and 5B; two rows of the smallest concavities 5', 5' on the upper portion and one row of the same concavities 5', 5' on the lower portion (FIG. 5A); or large concavities 5, 5 of an identical size (FIG. 5B).

It is clearly understood that the above embodiment is only illustrative and not restrictive in any sense. The spirit and scope of the present invention is limited only by the terms of the appended claims.

What is claimed is:

1. An endo-osseous implant, for embedding in dental alveoli, said implant comprising a plurality of concave surfaces on a tubular wall of a cylindrical main body, wherein each said concave surface has a shape of a double hemisphere consisting of an upper hemisphere of greater diameter and a lower hemisphere of smaller diameter.

2. An endo-osseous implant in accordance with claim 1, wherein fine notches are formed on said tubular wall of said cylindrical main body including said plurality of double hemispherical concave surfaces.

3. An endo-osseous implant in accordance with claim 1, wherein said cylindrical main body has an upper portion, such that said upper portion of said cylindrical main body in contact with gingiva is covered with a polycrystal ceramic layer.

4. An endo-osseous implant comprising
a substantially tubular main body having a top and a bottom and a tubular surface therebetween, and adapted for embedding in dental alveoli,
a plurality of concave surfaces disposed on said tubular outer surface of said main body, and
first receiving means located at the top of said main body for receiving an implanting instrument and for receiving and mounting a prosthetic holder,
wherein each said plurality of concavities comprises a substantially double hemispherical shape.

5. An endo-osseous implant according to claim 1 wherein said main body comprises fine notches located substantially throughout the entire outer surface of said cylindrical main body.

6. An endo-osseous implant according to claim 4 wherein at least a portion of said main body comprises a polycrystal ceramic layer forming said tubular outer surface.

7. An endo-osseous implant according to claim 4 wherein said main body is composed of titanium.

8. An endo-osseous implant according to claim 4 wherein said first receiving means comprises a female screw-type member for receiving the mating portion of a male-type screw.

9. An endo-osseous implant according to claim 4 wherein said main body further comprises
second receiving means having spiral threads for embedding said main body of said implant in said dental alveoli, and
a hemispherical concave recess in the bottom of said main body.

10. An endo-osseous implant according to claim 4 further comprising
a prosthesis holder having a top portion and a bottom portion,
said top portion comprising a receptacle for fixedly attaching a prosthetic unit, and
said bottom portion comprising a tapered member having spiral threads for fixedly attaching said prosthesis holder to said first receiving means of said main body.

11. An endo-osseous implant for embedding in dental alveoli, said implant comprising
a cylindrical main body having a top and a bottom and a tubular wall having an outer surface therebetween, said main body adapted for embedding in dental alveoli,
a plurality of concavities disposed on an outer surface of said tubular wall of said main body,
first receiving means located at the top of said main body for receiving an implanting instrument and for receiving and mounting a prosthetic holder, and
second receiving means located on a lower portion of said main body and having spiral threads for embedding said main body of said implant in said dental alveoli,
wherein said plurality of concavities include a plurality of double hemispherical shape concavities.

12. An endo-osseous implant in accordance with claim 11, wherein said main body further comprises a double hemispherical concave recess in said bottom of said main body.

13. An endo-osseous implant in accordance with claim 11, wherein said main body further comprises a hemispherical concave recess in the bottom of said main body.

14. An endo-osseous implant in accordance with claim 11, wherein said first receiving means comprises a female screw-type member for receiving the mating portion of a male-type screw.

15. An endo-osseous implant in accordance with claim 11, further comprising
a prosthesis holder having a top portion and a bottom portion, said top portion comprising a receptacle for fixedly attaching a prosthetic unit, and said bottom portion comprising a tapered member having spiral threads for fixedly attaching said prosthesis holder to said first receiving means of said man body.

16. An endo-osseous implant in accordance with claim 11, wherein said main body comprises fine notches located substantially throughout said outer surface of said tubular wall of said cylindrical main body.

17. An endo-osseous implant in accordance with claim 11, wherein at least a portion of said main body directly in contact with gingiva is covered with a polycrystal ceramic layer.

18. An endo-osseous implant in accordance with claim 17, wherein said plurality of concavities include relatively small-sized concavities disposed immediately below said polycrystal ceramic layer.

19. An endo-osseous implant in accordance with claim 11, wherein said main body is composed of titanium.

20. An endo-osseous implant according to claim 11 wherein said double hemispherical concavities have an upper hemisphere of greater diameter and a lower hemisphere of a smaller diameter.

* * * * *